US008644754B2

(12) United States Patent
Brown (10) Patent No.: US 8,644,754 B2
(45) Date of Patent: *Feb. 4, 2014

(54) METHOD AND APPARATUS FOR INTERACTIVELY MONITORING A PHYSIOLOGICAL CONDITION AND FOR INTERACTIVELY PROVIDING HEALTH-RELATED INFORMATION

(75) Inventor: Stephen J. Brown, Woodside, CA (US)

(73) Assignee: Robert Bosch Healthcare Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/609,468

(22) Filed: Dec. 12, 2006

(65) Prior Publication Data

US 2007/0156457 A1    Jul. 5, 2007

Related U.S. Application Data (60) Continuation of application No. 10/673,045, filed on Sep. 26, 2003, which is a continuation of application No. 09/971,785, filed on Oct. 4, 2001, now abandoned, which is a continuation of application No. 09/119,546, filed on Jul. 20, 1998, now Pat. No. 6,330,426, which is a continuation-in-part of application No. 08/953,883, filed on Oct. 20, 1997, now abandoned, which is a continuation-in-part of application No. 08/757,129, filed on Dec. 3, 1996, now Pat. No. 6,144,837, which is a continuation-in-part of application No. 08/334,643, filed on Nov. 4, 1994, now Pat. No. 5,601,435, said application No. 09/119,546 is a continuation of application No. 08/958,786, filed on Oct. 29, 1997, now Pat. No. 5,913,310, which is a continuation-in-part of application No. 08/857,187, filed on May 15, 1997, now Pat. No. 5,918,603, which is a division of application No. 08/247,716, filed on May 23, 1994, now Pat. No. 5,678,571.

(51) Int. Cl.
G09B 5/00    (2006.01)

(52) U.S. Cl.
USPC .......................................... 434/350; 434/322

(58) Field of Classification Search
USPC .................... 434/236, 262, 350, 307 R, 322; 600/300, 316; 702/19
See application file for complete search history.

(56) References Cited

U.S. PATENT DOCUMENTS 3,808,502 A    4/1974    Babilius
4,110,918 A    9/1978    James et al.

(Continued)

FOREIGN PATENT DOCUMENTS

WO    WO-93/02622    2/1993
WO    WO-94/16774    8/1994

OTHER PUBLICATIONS

Introducing the Next Generation of About Your Diabetes, U.S. Pharmacopical Convention and American Diabetes Association, (1993).

(Continued)

Primary Examiner — Kang Hu
(74) Attorney, Agent, or Firm — Maginot, Moore & Beck (57) ABSTRACT

An interactive health monitoring system. A multimedia processor is a electronic apparatus comprising a microprocessor, hardware, software, and a modem. One or more physiological data monitors are coupled to provide a signal representative of a user's physiological parameter to the multimedia processor through an isolated interface circuit. A hand-held program controller with directional buttons is operated by the user to control the various functions of the multimedia processor. A television is coupled to the multimedia processor to provide sound and a video display based upon output signals from the multimedia processor. Software necessary for the system and medical information are downloaded from a remote server based upon the user's operation of the hand-held program controller and also based upon predetermined software routines and data stored within the system.

23 Claims, 6 Drawing Sheets

(56) References Cited

U.S. PATENT DOCUMENTS

| | | | |
|---|---|---|---|
| 4,130,881 A | | 12/1978 | Haessler et al. |
| 4,237,344 A | * | 12/1980 | Moore ............................ 379/38 |
| 4,347,851 A | | 9/1982 | Jundanian |
| 4,360,345 A | | 11/1982 | Hon |
| 4,539,435 A | * | 9/1985 | Eckmann ........................ 379/76 |
| 4,576,578 A | | 3/1986 | Parker et al. |
| 4,700,055 A | * | 10/1987 | Kashkashian, Jr. ........... 235/379 |
| 4,729,381 A | | 3/1988 | Harada et al. |
| 4,749,354 A | | 6/1988 | Kerman |
| 4,779,199 A | | 10/1988 | Yoneda et al. |
| 4,796,639 A | | 1/1989 | Snow et al. |
| 4,803,625 A | | 2/1989 | Fu et al. |
| 4,858,617 A | | 8/1989 | Sanders |
| 4,907,973 A | | 3/1990 | Hon |
| 4,926,325 A | * | 5/1990 | Benton et al. ..................... 705/39 |
| 4,933,873 A | | 6/1990 | Kaufman et al. |
| 4,952,928 A | * | 8/1990 | Carroll et al. .............. 340/10.41 |
| 5,019,974 A | | 5/1991 | Beckers |
| 5,024,225 A | | 6/1991 | Fang |
| 5,025,374 A | | 6/1991 | Roizen et al. |
| 5,056,059 A | | 10/1991 | Tivig et al. |
| 5,120,230 A | | 6/1992 | Clark et al. |
| 5,222,020 A | | 6/1993 | Takeda |
| 5,226,431 A | | 7/1993 | Bible et al. |
| 5,277,197 A | | 1/1994 | Church et al. |
| 5,307,263 A | | 4/1994 | Brown |
| 5,377,258 A | * | 12/1994 | Bro .......................... 379/106.02 |
| 5,454,722 A | | 10/1995 | Holland et al. |
| 5,497,411 A | * | 3/1996 | Pellerin ........................ 455/411 |
| 5,497,772 A | * | 3/1996 | Schulman et al. ............. 600/347 |
| 5,507,288 A | | 4/1996 | Bocker et al. |
| 5,596,994 A | * | 1/1997 | Bro ................................ 600/545 |
| 5,597,307 A | | 1/1997 | Redford et al. |
| 5,601,435 A | | 2/1997 | Quy |
| 5,624,265 A | | 4/1997 | Redford et al. |
| 5,678,571 A | | 10/1997 | Brown |
| 5,722,418 A | * | 3/1998 | Bro ................................ 600/545 |
| 5,791,342 A | * | 8/1998 | Woodard ....................... 600/300 |
| 5,792,047 A | * | 8/1998 | Coggins ........................ 600/300 |
| 5,954,641 A | * | 9/1999 | Kehr et al. ..................... 600/300 |
| 6,011,991 A | * | 1/2000 | Mardirossian ................ 600/544 |
| 6,039,688 A | * | 3/2000 | Douglas et al. ............... 600/300 |
| 6,108,665 A | * | 8/2000 | Bair et al. ................... 707/104.1 |
| 6,144,837 A | | 11/2000 | Quy |
| 6,249,809 B1 | * | 6/2001 | Bro ................................ 709/217 |
| 6,334,778 B1 | | 1/2002 | Brown |
| 2003/0126593 A1 | | 7/2003 | Mault et al. |
| 2004/0106855 A1 | | 6/2004 | Brown et al. |

OTHER PUBLICATIONS

Shandle, Jack, "Who Will Dominate the Desktop in the 90's?", , Electronics, Feb. 1990, pp. 48-50. (3 pages) Cited by 2 patents.
Alere Medical Inc's First Supplemental Response to Plaintiffs Amended Interrogatory No. 2. Jun. 20, 2008.
U.S. Appl. No. 90/010,053—Order Granting Request for Ex Parte Reexamination, Jan. 18, 2008.
U.S. Appl. No. 90/009,237_Request_for_Re-examination_5601435_Aug. 1, 2008.

* cited by examiner

Means of monitoring a medical condition interfaced to multimedia processor via remote connection through telephone line and remote server

Figure 4

Monitoring means transmits monitoring data to multimedia processor via wireless paging network through remote server to television set-top processor

METHOD AND APPARATUS FOR INTERACTIVELY MONITORING A PHYSIOLOGICAL CONDITION AND FOR INTERACTIVELY PROVIDING HEALTH-RELATED INFORMATION

PRIORITY CLAIM

This application is a Continuation of application Ser. No. 10/673,045, filed Sep. 26, 2003, which is a Continuation of application Ser. No. 09/971,785, filed Oct. 4, 2001, now abandoned, which is a Continuation of application Ser. No. 09/119,546 filed Jul. 20, 1998, now U.S. Pat. No. 6,330,426, issued Dec. 11, 2001, which is a Continuation-In-Part of application Ser. No. 08/953,883 filed Oct. 20, 1997, now abandoned, which is a Continuation-In-Part of Ser. No. 08/757,129 filed Dec. 3, 1996, now U.S. Pat. No. 6,144,837 issued Nov. 7, 2000, which is a Continuation-In-Part of U.S. application Ser. No. 08/334,643 filed on Nov. 4, 1994, now U.S. Pat. No. 5,601,435 issued Feb. 11, 1997.

Application Ser. No. 09/119,546 filed Jul. 20, 1998, is also a Continuation of application Ser. No. 08/958,786, filed Oct. 29, 1997, now U.S. Pat. No. 5,913,310, issued Jun. 22, 1999, which is a Continuation-In-Part of application Ser. No. 08/857,187, filed May 15, 1997, now U.S. Pat. No. 5,918,603, issued Jul. 6, 1999, which is a Divisional of application Ser. No. 08/247,716, filed May 23, 1994, now U.S. Pat. No. 5,678,571, issued Oct. 21, 1997.

All of the above applications are herein incorporated by reference.

FIELD OF THE INVENTION

This invention relates to the field of health monitoring devices and methods of providing health care information. More specifically, the invention relates to educational and interactive health monitoring devices.

BACKGROUND OF THE INVENTION

Virtually everyone in the modern world is touched by the high cost of health care. With rising costs, fewer and fewer people can afford an optimal level of contact with a physician for treatment of health conditions or preventative care. This situation may lead many members of the population who are in need of health care to believe they cannot afford it. These persons are less likely to seek proper health care when needed.

Further, despite great advances in the field of medicine, there may still be some members of the population who feel threatened by or who harbor a distrust or fear of health care professionals or institutions, for any number of reasons. These persons are also less likely to seek proper health care when needed.

The two factors mentioned above: the high cost of health care and distrust or fear of health care professionals or institutions, may combine in members of the population to prevent such persons from seeking out and obtaining adequate health care.

Therefore, what is needed is a device which can reduce health care costs by performing some functions of a health care professional and at the same time reduce possible distrust of health care professionals and institutions by providing health care functions to a user in a patient-friendly and non-threatening manner.

The prior art discloses devices that monitor health related parameters. For example, U.S. Pat. No. 5,307,263 discloses a modular, microprocessor-based, health monitoring system. The hand-held unit has a display screen, a control button pad, interchangeable program cartridges and sensors for monitoring a variety of health care data. The program cartridges may include motivational and educational material related to use of the device, including step-by-step instructions. Acquired data may be transmitted to a data management unit via an interface cable and to a clearinghouse via telephone lines. A program cartridge for monitoring glucose levels and a glucose sensor is disclosed having the purpose of caring for children with diabetes. However, this device has the disadvantage of having a relatively small liquid crystal display screen, a limited ability to process and store data due to its small size, and limited ontime due to its battery power. Because this invention is directed to chronic ailments, its educational capabilities are likely limited to teaching how to use the device and to teaching about those chronic ailments to which it is directed.

Another example, disclosed in U.S. Pat. No. 4,803,625, is a personal health monitor that measures a patient's weight, temperature, blood pressure and ECG waveform. A plurality of monitors may be coupled to a central computer via telephone lines. The central computer may prompt the patients to take medication, measure certain health parameters, supply answers to selected questions or determine patient symptoms based on patient responses to questions. The monitor transmits patient data to the central computer. The central computer compares collected patient data to expected values and triggers an alarm if the data falls outside a predetermined range. However, that system is not interactive. It is not interactively controlled by the user and it does not have the capability to provide health-related information.

Yet another example can be found in U.S. Pat. No. 5,024,225 which discloses a personal health monitor and its enclosure. The object of that invention is to provide an enclosure for a health monitor such as the one described in U.S. Pat. No. 4,803,625, discussed above. A disadvantage of this device is that it requires the use of a standard lap top computer as the processing unit which increases the cost of the device.

None of the above-mentioned patented devices benefit from the versatility of enhanced sound, video, network capabilities and cost effectiveness of a multimedia processor.

SUMMARY OF THE INVENTION

The present invention is a method of and a system for providing interactive health-related educational materials to a patient. It is an object of the present invention to reduce health care costs by performing some functions of a health care professional. It is a further object of the present invention to achieve the abovementioned objects through education obtained in an enjoyable and interactive manner. These and other objects of the invention will be described more fully in the remainder of the specification.

In the preferred embodiment of the present invention, a multimedia processor is coupled to one or more physiological data monitors to receive a signal representative of a user's physiological parameter, such as blood sugar level, to the multimedia processor through an infra-red serial input/output port. A hand-held program controller having directional buttons is operated by the user to control the various functions of the multimedia processor. The signals emitted from hand-held program controller is transmitted to the multimedia processor through one of a plurality of input/output ports. A television is also coupled to the multimedia processor through another one of the input/output ports to provide sound and a video display based upon output signals from the multimedia processor.

Furthermore, the multimedia processor is coupled to the remote server through a computer network such as the Internet. The multimedia processor can be coupled to the computer network through a telephone line or through satellite television transmission. Health-related educational materials, as well as other health related information, are stored in the remote server and can be downloaded from the remote server via the computer network.

Preferably, a Smart-Card slot is coupled to the multimedia processor. The smart-card is programmed with a user code, the health status of the user and the location of the remote server where the health-related educational materials are stored. The user code is used by the system for identifying the user and for downloading appropriate health-related education materials depending on the user's profile.

The multimedia processor may also be coupled to an optional CD-ROM player for playing interchangeable compact disks (CD-ROM) that can be used to store software and other health-related educational materials.

In an alternate embodiment of the present invention, a multimedia processor is electronically imprinted with a digital signature which is readable by a remote server. The remote server will be able to determine the identity of the user based on the digital imprint and download appropriate health-related educational materials accordingly.

In a further alternate embodiment of the present invention, one or more physiological data monitors are coupled to a remote server via a communications means where physiological data are transmitted directly to the remote server. The communications means can comprise any means known in the art, such as telephone lines and coaxial cables. The remote server processes and stores the physiological data and transmits the data to the multimedia processor via a computer network.

DETAILED DESCRIPTION OF THE PREFERRED EMBODIMENT

Figure 1:
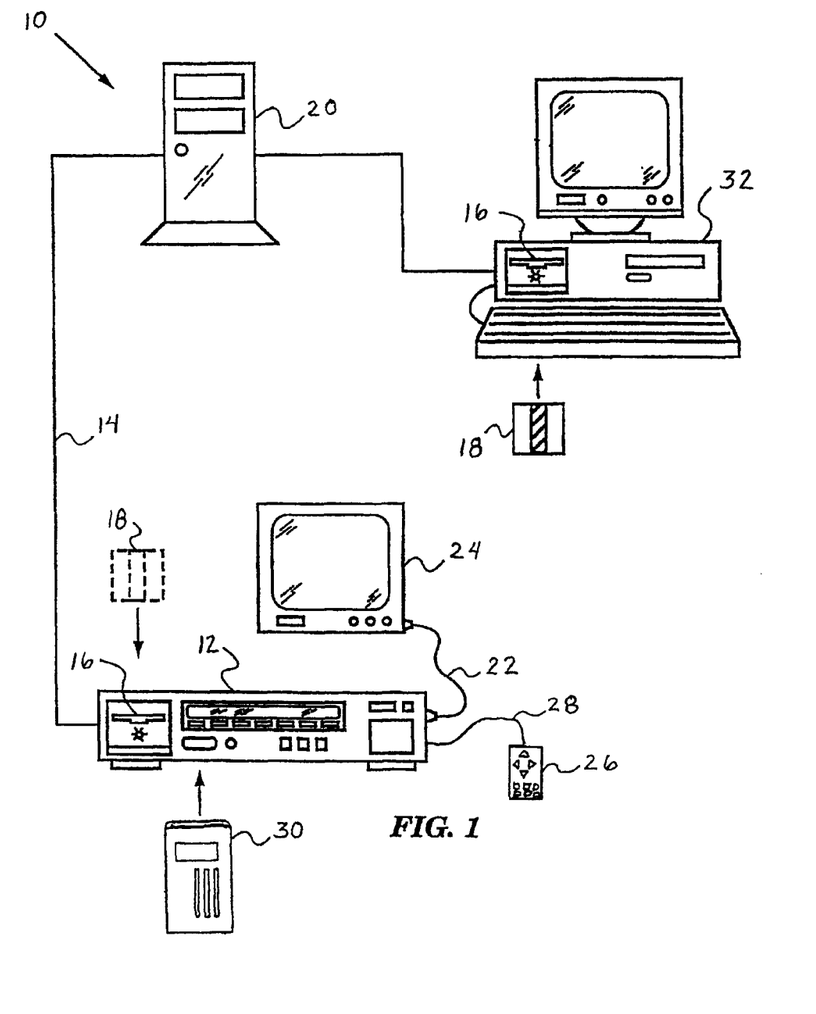
FIG. 1 shows a diagram of the preferred embodiment the present invention.

FIG. 1 shows a diagram 10 of the preferred embodiment of the present invention. In the preferred embodiment, the multimedia processor 12 is an internet terminal, such as the Internet Unit developed by Philips-Magnavox. The multimedia processor 12 is somewhat smaller in size than a typical video cassette recorder and sits on top of a television set. The multimedia processor 12 preferably comprises a microprocessor, hardware, software, a modem for connecting to a computer network 14 such as the Internet, and an ISO Smart-Card slot 16 which supports ISO compliant smart cards 18. Health-related educational materials are stored in a series of "web pages" in the remote server 20, and can be downloaded.

In addition, the multimedia processor 12 preferably has expansion ports to support additional user interface and other devices, such as keyboards, joysticks, trackballs, and to accept add-on circuits for enhanced sound, video, or processing performance.

Figure 2:
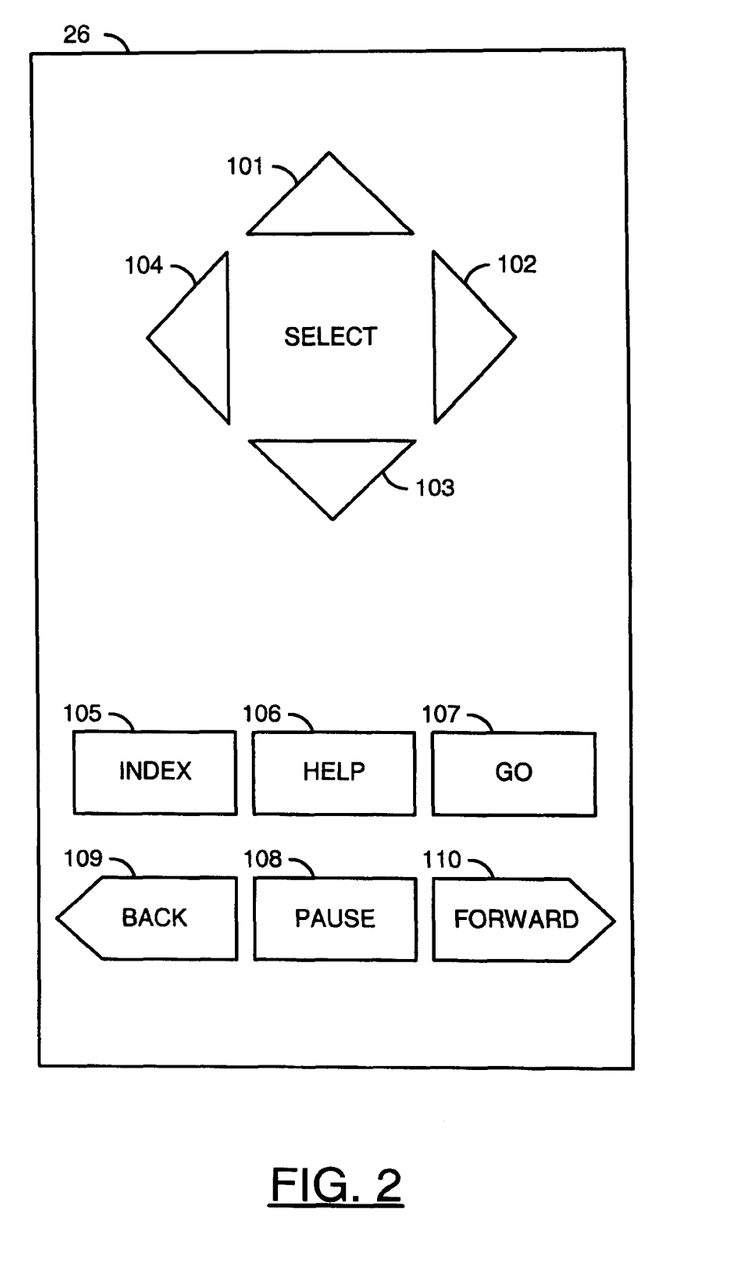
FIG. 2 shows a detailed diagram of the hand-held program controller of the present invention.

The multimedia processor 12 is coupled by a television interface cable 22 to a television 24 of the conventional type or to a television having enhanced video or sound capabilities. The multimedia processor 12 supplies electronic information to the television 24 through the television interface cable 22 to enable the television 24 to produce appropriate images on the television screen and to enable the television 24 to project appropriate audio sounds from the television speaker or speakers. Stereo sound effects may be employed in those televisions having stereo capability. In addition, auxiliary speakers or sound amplification devices may be coupled to the television 24. The multimedia processor 12 is also coupled to a program controller 26 by a control interface cable 28. The program controller 26 enables the user to make selections and to control the functions of the health monitoring system. The program controller 26 is also shown in FIG. 2 and is described in detail below.

Alternatively, the multimedia processor 12 can be mounted internally to the housing of a display unit.

The multimedia processor 12 is also coupled to a physiological data monitor 30 through an infra-red serial port. The physiological data monitor 30 is coupled to the user's body to obtain electrical signals representative of a physiological parameter. The physiological data monitor 30 is coupled to the multimedia processor 12 through an interface device. The interface device includes hardware and software necessary to receive signals from the physiological data monitor 30 by means of the signal receiver, to perform signal conditioning or processing by means of the processor and the convertor, to control the multimedia processor 12 by means of the multimedia controller, and to provide signals representative of a physiological parameter to the multimedia processor 12 through an interface cable. Such signal processing may include digital to analog conversion, analog to digital conversion, digital reformatting, and signal scaling and may be based upon the system hardware, software, user input or upon requirements of the physiological data monitor.

In addition, the multimedia processor 12 may provide control signals to the interface device through the infra-red port based upon the hardware and software in the multimedia processor and upon the user's input to the program controller 26. Additionally, the program controller 26 may be coupled to provide control signals directly to the interface device.

As an example only, the present invention may comprise an blood glucose level indicator, such as "Accucheck Easy," which is manufactured by Boehringer-Mannheim. Other standard or modified patient monitoring equipments, such as a blood pressure cuff called "Dynamap" made by Johnson & Johnson, can also be used. These patient monitoring equipments often have an RS-232 port or analog output jacks. Therefore, to save manufacturing costs, the present invention includes the ability to interface with such types of connectors by including compatible connectors and related hardware in the interface device. Each of the various physiological data monitors 30 are interchangeable and each may have corresponding software stored on the remote server 20.

Educational content are stored in the remote server 20 in the series of "web pages". These web pages are transmitted to the multi-media processor 12 after the user logs in. The user can log in using several different methods. First, the user can use a pre-programmed Smart-Card 18 containing a patient code and health status information to log on. Depending on the patient code and health status information, the remote server 20 will download appropriate disease management materials. Alternatively, the multimedia processor 12 can be electronically imprinted with a "digital signature", such as the serial number, readable by the remote server 20. The remote server 20 can then look up a user directory comprising records of users and serial numbers of the multimedia processors to retrieve a profile of the user. Based upon the user profile, the remote server 20 can then download an appropriate set of health-related educational materials tailored to the user. Further alternatively, the user may access the system by entering a login name and a corresponding password.

To better illustrate the present invention, an example is described of how the system of the present invention operates to educate a patient with diabetes and to measure his blood glucose level. First, a user sets up the system by connecting the multimedia processor 12 to a television 24 and to a telephone jack. Next, the user inserts his pre-programmed Smart-Card 18 into the Smart-Card slot 16, and turns the system on. Then, the multimedia processor 12 reads the user identification and health status information off the Smart-Card 18, and transmits this information to the remote server 20. The remote server 20, upon receiving this information and recognizing the user as a diabetic, downloads educational materials relating to diabetes as well as step-by-step instructions of how to hook up a blood glucose level monitor. The user, following the on-line instructions, sets up the glucose level indicator and takes the measurements. The system then takes measurements of physiological parameters, stores the measurements in the remote server 20, and display of the results on the television screen. In this case, for example, the health monitoring system may display on the television screen a moving or still image or images and possibly audio signals to explain what a normal blood glucose level should be, what kinds of food should the user avoid, and guide the user through the steps necessary to take blood glucose level measurements.

The data taken by the system is uploaded to the remote server 20. Then, the health monitoring system displays the results of the measurements. In this case, the user's blood glucose level may be displayed along with a comparison of the user's previous record of blood glucose level. Under certain configurations, such information can be stored in memory on the user's Smart-Card 18. The health monitoring system can also compare the user's measurements with previously stored measurements of the same user's blood glucose level or with measurements representative of a normative physiological parameter. Based upon these comparisons, the system can guide the user through additional measurements, store information for later retrieval or downloading, recommend that the user seek the services of a health care professional, ask questions of the user, give advice in areas such as the user's diet and exercise habits, and so forth. In addition to the above, the health monitoring system can provide functions related to blood pressure, glucose levels, pulse rate, kidney function, and so forth.

Furthermore, the remote server 20 can collect the physiological data for storage and access by health-care professionals. It is desirable for physiological data of the user to be accessible by doctors because those data will allow the doctors to quickly pinpoint to problem areas. It is particularly useful to chronically ill patients where an accurate and detailed record will be kept even when they are recovering at home.

In an alternate embodiment, information obtained from the patient can be automatically downloaded to a health-care professional's computer 32. In this way, a health-care professional treating a patient will be provided with a detailed medical record of the patient. This detailed medical record will allow doctors and other healthcare professionals to respond to any changes in the patient's medical conditions efficiently and expediently, thus effecting a further savings in medical resources.

FIG. 2 shows a hand-held program controller 26. The program controller 26 comprises a variety of push button switches. The push button switches are coupled to be activated by control buttons 101, 102, 103, 104, 105, 106, 107, 108, 109, and 110 which are manipulated by the user for controlling the health monitoring system. The program controller has a group of directional control buttons 101, 102, 103 and 104 in the center of which is printed the label "SELECT." The button 105 is printed with the label "INDEX." The button 106 is printed with the label "HELP." The button 107 is printed with the label "GO." The button 108 is printed with the label "PAUSE." The button 109 has the label "BACK" printed on or near it. The button 110 has the label "FORWARD" printed on or near it. The specific configuration of the buttons and labels is by way of example only and it should be apparent that any number of alternate configurations of buttons, keys, or different labels would suffice to achieve the objects of the program controller.

Figure 3:
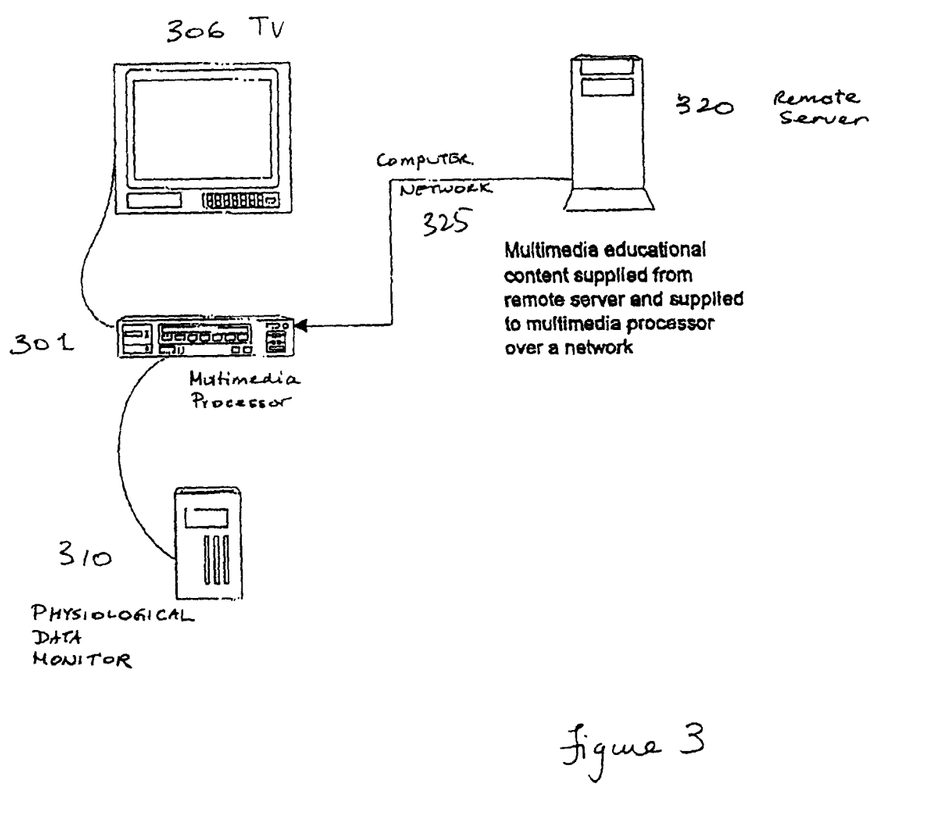
FIG. 3 shows a diagram of an alternate embodiment of the present invention where the user is identified by a digital signature of the multimedia processor.

FIG. 3 illustrates a diagram of an alternate embodiment of the present invention. A multimedia processor 301 which comprises a microprocessor, hardware, software and an optional CD-ROM device is shown. The multimedia processor 301 further comprises a communications port for coupling to a remote server 320. Data and software modules that are medically or health-related are stored in the memory store of the remote server 320, and can be downloaded to the multimedia processor 301.

Figure 4:
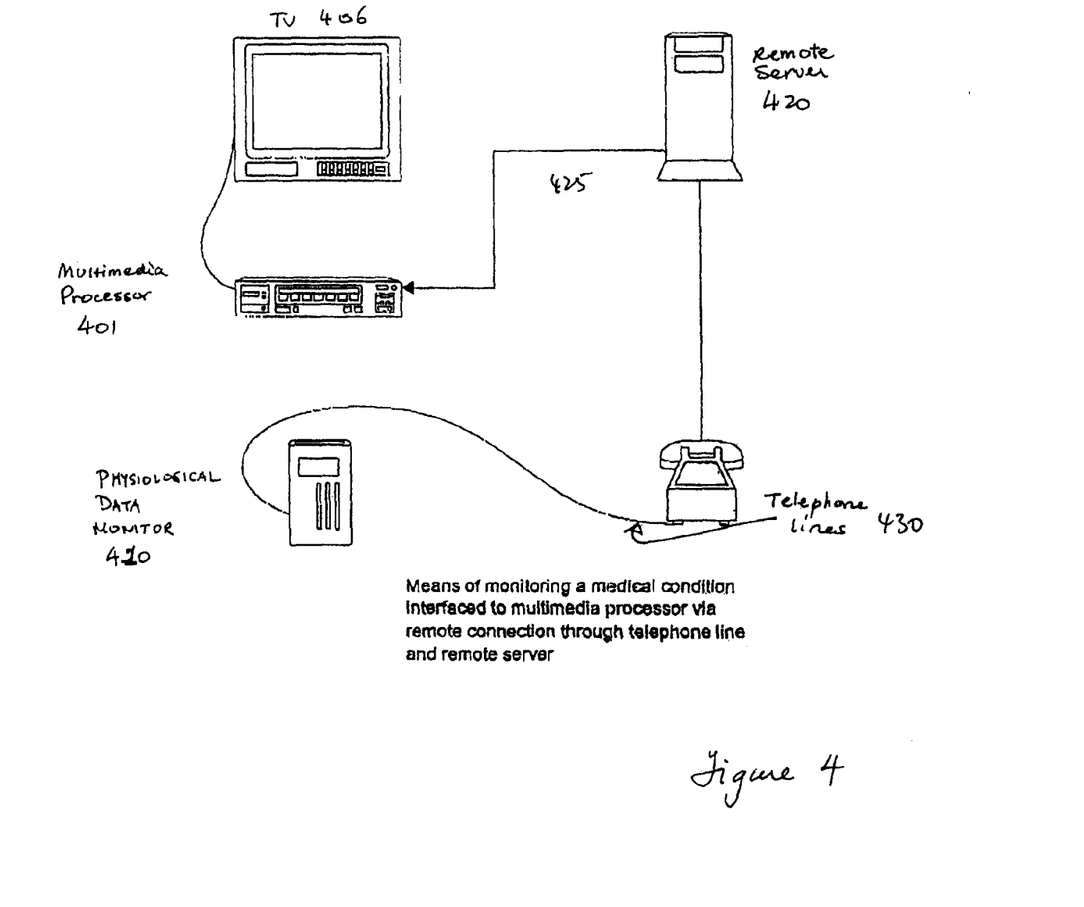
FIG. 4 shows a diagram of an alternate embodiment of the present invention where a physiological data monitor is coupled directly to a remote server via a telephone line.

In FIG. 4, an alternate embodiment of the present invention is shown. In this embodiment, a physiological data monitor 410 is coupled to a remote server 420 via a telephone line 430. The interface device which converts the signals from the physiological data monitor is embedded within the physiological data monitor and is not shown. The physiological data monitor 410 transmits the collected data via the telephone line 430 to the remote server which stores them and retransmits them to the multimedia processor by ways of a computer network 425.

Figure 5:
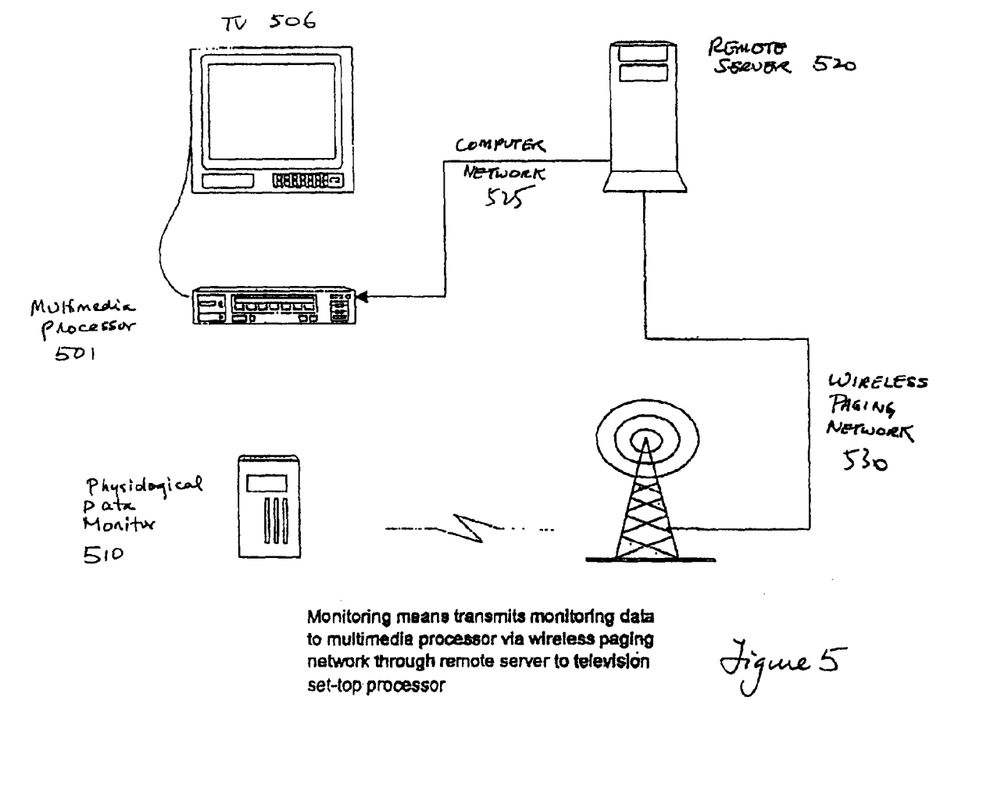
FIG. 5 shows a diagram of an alternate embodiment of the present invention where a physiological data monitor is coupled to a remote server via a wireless paging network.

In FIG. 5, a second alternate embodiment of the present invention is shown. In this embodiment, the physiological data monitor 510 has the capability to transmit data to a remote server 520 via a wireless paging network 530. The physiological data is collected by the physiological data monitor and converted by an interface device (not shown) into radio signals to be received by a wireless paging network. The remote server will reconstitute the radio signals into digital form to be stored and retransmitted to the multimedia processor 501 by way of a computer network 525.

Figure 6:
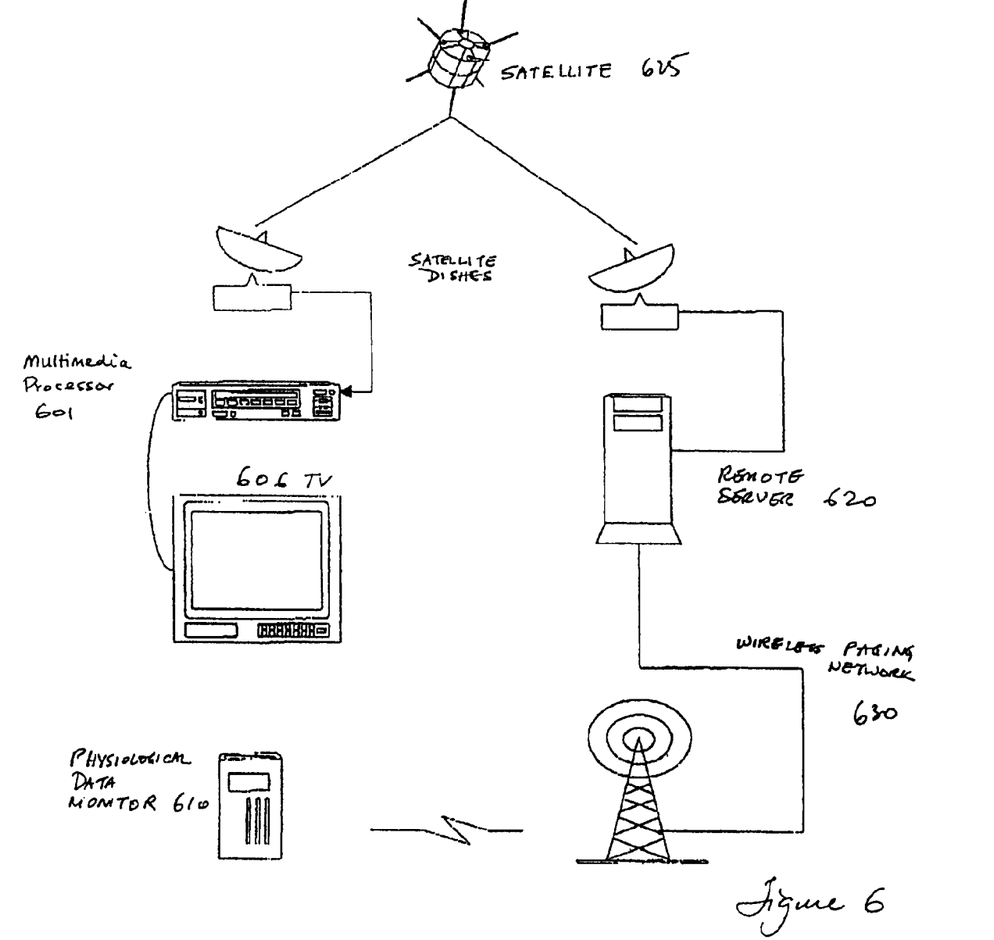
FIG. 6 shows a diagram of coupling a multimedia processor with a remote server through a satellite TV transmission.

FIG. 6 shows a diagram of the present invention showing how health-related educational materials and other data can be transmitted from a remote server to a multimedia processor 601 via a satellite 625, and showing how physiological data can be transmitted from a physiological data monitor 610 to the remote server 620 via a wireless communications network 630.

The following example shows one implementation of the present invention as it applies to working with a diabetes patient through MEDTV™ over the world wide web of the internet. MEDTV is a trademark of Raya Systems, Inc., of Mountain View, Calif.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention. Specifically, it will be apparent that to one of ordinary skill in the art that the device of the present invention could be implemented in several different ways and the apparatus disclosed above is only illustrative of the preferred embodiment of the invention and is in no way a limitation.

The invention claimed is:

1. A system of providing information to an individual comprising:
   a processor unit comprising a memory slot and a physiological data monitoring device interface, said processor unit configured to (i) present material to the individual, (ii) receive a plurality of responses from the individual and (iii) read an identification code and health status information of the individual from a memory device while said memory device is connected to said memory slot;
   a server configured to (a) communicate with the processor unit via at least one first communication network and (b) access a non-transitory computer readable storage medium storing a plurality of media programs, wherein (i) the server is remotely situated from the processor unit, (ii) the server is configured to receive the identification code and the health status information from the processor unit and communicate at least a first one of the media programs to the processor unit based upon (a) the identification code input by said individual, (b) the health status information received from the processor unit and (c) a destination address programmed on the medium by a physician prior to said individual receiving said processor unit, (iii) the processor unit is configured to communicate the responses received from the individual to the server via the first communication network, (iv) the identification code is used by the server to direct the first media program to a particular individual or a group of individuals, (v) at least a second one of the media programs communicated by the server to the processor unit conveys a positive reinforcement where a corresponding one of the responses is indicative of compliance with a health regimen and (vi) the media programs comprise video programs with audio; and
   a physiological data monitoring device configured to communicate with the processor unit via the physiological data monitoring device interface.

2. The system according to claim 1, wherein at least a third one of the media programs communicated from the server to the processor unit comprises educational content where the corresponding one of the responses is indicative of non-compliance with said health regimen.

3. The system according to claim 1, wherein the physiological data monitoring device is coupled to the processor unit by an infra-red connection.

4. The system according to claim 1, further comprising a television coupled to said processor unit and configured to present the media programs received at the processor unit from the server.

5. The system according to claim 1, further comprising a hand held controller coupled to said processor unit.

6. The system according to claim 1, wherein said processor unit is configured to communicate with a smart card storing the identification code, the health status information, and location information of said server in the first communication network.

7. The system according to claim 1, further comprising a healthcare professional computer remotely situated from the server and the processor unit, wherein the healthcare professional computer is configured to communicate with the server via at least one second communication network.

8. The system according to claim 1, wherein at least one of the media programs conveys proper self-management feedback.

9. The system according to claim 1, wherein at least one of the media programs conveys a motivation.

10. The system according to claim 1, wherein at least one of the media programs conveys supportive feedback.

11. The system according to claim 1, wherein at least one of the media programs conveys a positive effect.

12. A system of monitoring a condition of an individual comprising:
    a processor unit comprising a memory slot and a physiological data monitoring device interface, said processor unit configured to (i) present material to the individual and (ii) read an identification code and health status information of the individual from a memory device while said memory device is connected to said memory slot;
    a server configured to communicate with the processor unit via at least one communication network, wherein (i) the server is remotely situated from the processor unit, (ii) the server is configured to communicate information to the processor unit, (iii) the server is configured to receive the identification code and the health status information of the individual from the processor unit via the communication network, and (iv) the information communicated by the server to the processor unit comprises one or more media programs based on (i) the identification code input by said individual, (b) and the health status information received from the processor unit and (c) a destination address programmed on the memory device by a physician prior to said individual receiving said processor unit; and
    a physiological data monitoring device configured to communicate with the server through both (a) the processor unit via the physiological data monitoring device interface and (b) the at least one communication network, wherein (i) the information communicated by the server to the processor unit is based on data communicated by the physiological data monitoring device to the server and (ii) at least one of the media programs comprises a video program with audio that conveys a positive reinforcement in response to the data.

13. The system according to claim 12, wherein the at least one communication network comprises a computer network.

14. The system according to claim 12, wherein the at least one communication network comprises a telephone network.

15. The system according to claim 12, wherein the at least one communication network comprises a cable network.

16. The system according to claim 12, further comprising a television coupled to said processor unit and configured to present the media programs received at the processor unit from the server.

17. The system according to claim 12, wherein the at least one communication network comprises a wireless network.

18. The system according to claim 12, wherein the physiological data monitoring device is configured to measure a physiological parameter of the individual.

19. The system according to claim 12, wherein the at least one communication network comprises a satellite network.

20. The system of claim 19, further comprising:
   a transmitter coupling the server to the satellite network; and
   a receiver coupling the processor unit to the satellite network.

21. A system of monitoring a condition of an individual comprising:
   a processor unit comprising a memory slot and a physiological data monitoring device interface, said processor unit configured to (i) present material to the individual, (ii) receive responses from the individual and (iii) read an identification code and health status information of the individual from a memory device while said memory device is connected to said memory slot;
   a server configured to (a) communicate with the processor unit via at least one communication network and (b) access a non-transitory computer readable storage medium storing a plurality of media programs, wherein (i) the server is remotely situated from the processor unit, (ii) the server is configured to receive the identification code and the health status information from the processor unit and communicate at least a first one of the media programs to the processor unit based upon (a) the identification code input by the individual, (b) and the health status information, and (c) a destination address programmed on the medium by a physician prior to said individual receiving said processor unit, (iii) the processor unit is configured to communicate the responses received from the individual to the server via the communication network, (iv) the identification code is used by the server to direct the first media program to a particular individual or a group of individuals, (v) at least a second one of the media programs communicated from the server to the processor unit conveys a positive reinforcement where a corresponding one of the responses is indicative of compliance with a health regimen and (vi) the media programs comprise video programs with audio; and
   a physiological data monitoring device configured to communicate with said server via both the processor unit and the at least one communication network, wherein the physiological data monitoring device communicates with the processor unit via the physiological data monitoring device interface.

22. The system according to claim 21, wherein the media programs comprise educational material concerning one or more health related topics selected from preventative measures, exercise, diet, lifestyle, health conditions, diseases, health consequences, health monitoring and self-care.

23. The system according to claim 21, wherein at least a third one of the media programs (i) communicated by the server to the processor unit and (ii) containing educational material is determined based on data communicated by the physiological data monitoring device to the server that indicates an inappropriate condition of the individual.

* * * * *